(12) United States Patent
Li et al.

(10) Patent No.: US 11,813,250 B2
(45) Date of Patent: Nov. 14, 2023

(54) TOPICAL FORMULATIONS CONTAINING MTOR INHIBITORS

(71) Applicant: Shanghai Aucta Pharmaceuticals Co., Ltd., Shanghai (CN)

(72) Inventors: Shoufeng Li, Basking Ridge, NJ (US); Yi Zhao, Monmouth Junction, NJ (US); Qiaolin Ren, Jericho, NY (US)

(73) Assignee: SHANGHAI AUCTA PHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 17/929,569

(22) Filed: Sep. 2, 2022

(65) Prior Publication Data
US 2023/0100760 A1 Mar. 30, 2023

Related U.S. Application Data

(63) Continuation-in-part of application No. PCT/IB2020/055930, filed on Jun. 23, 2020.

(60) Provisional application No. 62/984,000, filed on Mar. 2, 2020.

(51) Int. Cl.
| | | |
|---|---|---|
| A01N 37/00 | (2006.01) |
| A61K 31/215 | (2006.01) |
| A01N 37/12 | (2006.01) |
| A01N 37/44 | (2006.01) |
| A61K 31/24 | (2006.01) |
| A01N 25/00 | (2006.01) |
| A61K 31/436 | (2006.01) |
| A61P 17/00 | (2006.01) |
| A61K 9/00 | (2006.01) |
| A61K 9/06 | (2006.01) |
| A61K 47/06 | (2006.01) |
| A61K 47/12 | (2006.01) |
| A61K 47/14 | (2017.01) |
| A61K 47/20 | (2006.01) |
| A61K 47/22 | (2006.01) |
| A61K 47/44 | (2017.01) |

(52) U.S. Cl.
CPC .......... *A61K 31/436* (2013.01); *A61K 9/0014* (2013.01); *A61K 9/06* (2013.01); *A61K 47/06* (2013.01); *A61K 47/12* (2013.01); *A61K 47/14* (2013.01); *A61K 47/20* (2013.01); *A61K 47/22* (2013.01); *A61K 47/44* (2013.01); *A61P 17/00* (2018.01)

(58) Field of Classification Search
None
See application file for complete search history.

(56) References Cited

U.S. PATENT DOCUMENTS

| | | |
|---|---|---|
| 5,385,907 A | 1/1995 | Asakura et al. |
| 2013/0317053 A1 | 11/2013 | Kaneda et al. |
| 2020/0000778 A1 | 1/2020 | Kaupinen et al. |

FOREIGN PATENT DOCUMENTS

| | | |
|---|---|---|
| WO | 9924036 A1 | 5/1999 |
| WO | 2006029726 A1 | 3/2006 |
| WO | 2018126049 A1 | 7/2018 |
| WO | 2018129364 A1 | 7/2018 |

*Primary Examiner* — Layla Soroush
(74) *Attorney, Agent, or Firm* — FOX ROTHSCHILD LLP

(57) ABSTRACT

A formulation for topical delivery of mTOR inhibitors with extended shelf-life. The formulation comprises an mTOR inhibitor, a solvent capable of dissolving and stabilizing the inhibitor. The use of the formulation for the treatment of skin lesions and other topical diseases is also disclosed.

20 Claims, 1 Drawing Sheet

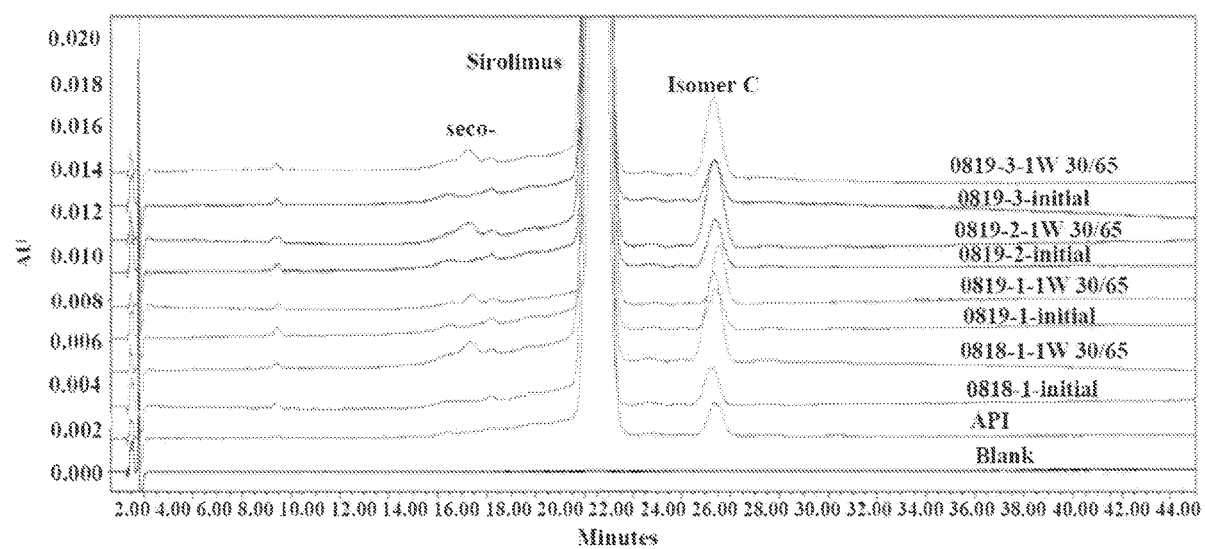

TOPICAL FORMULATIONS CONTAINING MTOR INHIBITORS

CROSS-REFERENCE TO RELATED APPLICATIONS

This application is a Continuation-in-part application of PCT/IB2020/055930 under 35 U.S.C. 111(a), filed on Jun. 23, 202, which claims the benefit of U.S. Provisional Patent Application No. 62/984,000, filed on Mar. 2, 2020, the contents of which are herein incorporated by reference into the subject application.

FIELD OF INVENTION

The present invention relates to a novel formulation of mTOR Inhibitors and methods for the treatment of dermatological diseases.

BACKGROUND

Sirolimus, also known as rapamycin, is the active ingredient in Wyeth's approved Rapamune® oral solution and tablets, and is obtained by fermentation with a strain of *Streptomyces hygroscopicus*. Sirolimus is an immunosuppressive agent indicated for the prophylaxis of organ rejection in patients aged ≥13 years receiving renal transplants.

Everolimus is a semi-synthetic macrolide immunosuppressant derived from sirolimus. It is the active ingredient in Novartis' approved Afinitor® oral tablet. The product is used in treatment of tuberous sclerosis complex including TSC-associated subependymal giant cell astrocytoma (SEGA), TSC-associated angiomyolipoma and TSC-associated lymphangioleiomyomatosis (LAM), but it has never been approved as a topical agent.

Both sirolimus and everolimus are poorly water-soluble. They are susceptible to oxidation. They inhibit IL-2 and other cytokines receptor-dependent signal transduction mechanisms, via action on mTOR (mammalian target of rapamycin), and thereby blocks activation of T and B cells. The serine-threonine kinase as a mTOR is downstream of PI3K-AKT pathway and is implicated in protein synthesis and cell cycle control. Sirolimus and everolimus has been shown to be an inhibitor of tumor growth in xenograft models of various human cancer cell lines. In xenograft models tested, the down-regulation of p70 S6 kinase (S6K), a kinase downstream from mTOR and involved in protein translation, has been directly related to their anti-tumor activity.

The immunosuppressive effect of everolimus was demonstrated in an in vitro assay, where everolimus blocked lymphocyte proliferation in response to a mitogenic stimulus. In Europe, everolimus is used as an immunosuppressant in organ transplant patients to prevent transplant rejection. Additionally, in in vitro assays, everolimus exhibited a direct inhibitory effect on mouse and human osteoclast formation and activity, and to a lesser extent Osteoblast differentiation.

Facial angiofibromas are disfiguring facial lesions, present in up to 80% of patients with tuberous sclerosis complex (TSC). Lesions arise in early childhood and in some patients, the lesions become confluent and can result in severe disfigurement. The typical facial angiofibromas are red to pink papules/nodules when they first appear, with a smooth, glistening surface. They are usually, but not always, bilaterally symmetrical, distributed over the centrofacial areas, particularly in the nasolabial folds, onto the cheeks in a butterfly fashion, and on the chin.

Recent elucidation of the complex signaling relationship between the tuberous sclerosis 1 (TSC1) and tuberous sclerosis 2 (TSC2) gene products and mTOR has led to an explosion of research related to the use of mTOR inhibitors, such as rapamycin and everolimus in TSC. The majority of patients with TSC have mutations in TSC1 or TSC2, resulting in constitutive activation of mTOR. Because the pathogenesis of the disease is mTOR hyperactivity, mTOR inhibitors have the potential to treat the underlying cause in TSC patients.

Current treatment options for facial angiofibromas include destructive approaches such as dermabrasion, surgical excision, and laser therapy. General anesthesia may be necessary depending on the individual's symptoms and ability to cope with the procedure, especially for those individuals with TSC who have severe learning disabilities. Although clinical case studies have shown therapeutic effect of mTOR inhibitor on the treatment of facial angiofibromas, the studies typically used grounded powder of drug tablets for topical application.

SUMMARY OF THE INVENTION

This patent document provides topical formulations of mTOR inhibitors. The formulations enables the penetration of superficial dermal layers of the epidermis to provide a therapeutically effective amount of the active ingredient. Meanwhile, the active ingredient remains stable for an extended period of time in the formulations, thus providing a convenient long term treatment option. In addition, it would greatly improve patient compliance and reduce healthcare burden because skin lesions, if untreated, can progress to the stage of hospitalization and even surgery.

An aspect of this patent document provides topical compositions or formulations of sirolimus or everolimus. The formulation can be in the form of, for example, ointment, cream, solution and suspension. In some embodiments, the formulation contains an effective amount of sirolimus or everolimus and a dermatologically carrier. In some embodiments, the effective amount of mTOR inhibitor in the formulation is 0.001% to 2% by weight. The dermatologically carrier is selected from emollient agent, emulsifying agent, thickening agent, preservative, permeation enhancer, buffering agent and solvent. In some embodiments, the emollient agent of the formulation is white petrolatum and mineral oil, the emulsifying agent is caprylocaproyl polyoxyl-8 glycerides, the thickening agent is glyceryl behenate and the solvent is DMSO and propylene carbonate.

Another aspect of the present disclosure provides a process for preparing a pharmaceutical ointment formulation comprising (a) dissolving sirolimus or everolimus in one or more solvents; (b) providing an ointment base; and mixing the product of step (a) with the product of step (b).

Another aspect of the present disclosure provides a method for treating TSC related skin lesions such as facial angiofibroma. The method includes applying topically the formulation to the diseased area once, twice, three times, four times, or as needed daily to provide targeted, localized, effective concentrations of agents. Typical side effects of systemic administration are reduced because the agents are not administered systemically.

DESCRIPTIONS OF DRAWINGS

FIG. 1 shows the HPLC chromatograms of Sirolimus, Seco-Rapamycin and Isomer C from Sirolimus Ointment.

DETAILED DESCRIPTION OF THE INVENTION

The present disclosure provides pharmaceutical compositions or formulations containing a suitable organic solvent for topical delivery of a therapeutic agent. The formulation can be in the form of a solution, a suspension, a foam, a spray, an ointment, a cream, and an aerosol. In comparison with conventional oral delivery route, the topical formulation disclosed herein bypasses portal circulation and hepatic first pass metabolism, therefore significantly reducing side effects associated with systemic administration. Moreover, the formulation effectively delivers the active ingredient to the diseased area and eliminates issues associate with gastrointestinal irritation in oral administration. Further, the stability of the active ingredient in the formation is maintained for an extended period of time.

While the following text may reference or exemplify specific embodiments of a formulation or method of treating a disease or condition, it is not intended to limit the scope of the embodiment or method to such particular reference or examples. Various modifications may be made by those skilled in the art, in view of practical and economic considerations, such as the components and their ratio in a solvent of the formulation and the effective amount in applying the formulation for treating a condition.

The articles "a" and "an" as used herein refers to "one or more" or "at least one," unless otherwise indicated. That is, reference to any element or component of the present invention by the indefinite article "a" or "an" does not exclude the possibility that more than one of the element or component is present.

The term "about" as used herein refers to the referenced numeric indication plus or minus 10% of that referenced numeric indication.

The term "subject" as used herein is intended to include human and non-human animals. Non-human animals include all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for tr1: 5eating human patients having a disorder that can be treated by augmenting the immune response.

"Treating" or "treatment of a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The term "effective amount" as used herein means that amount of a formulation or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Specific doses can be readily determined by one having ordinary skill in the art, using routine procedures.

The term "formulation" or "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical formulations or compositions are prepared by uniformly and intimately bringing the active ingredient into association with a liquid carrier or a finely divided solid carrier or both, and then, if necessary, shaping the product into the desired formulation. In the pharmaceutical formulation or composition the active ingredient is included in an amount sufficient to produce the desired effect upon the process or condition of diseases. Accordingly, the pharmaceutical formulation or composition described herein encompasses any formulation or composition made by mixing a compound of the present invention and a pharmaceutically acceptable carrier.

The term "pharmaceutically acceptable carrier" as used herein includes any and all solvents, dispersion media, coatings, antibacterial and antifungal agents, isotonic and absorption delaying agents, and the like that are physiologically compatible. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, penetration enhancers, emulsifiers, thickeners, emollients, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences. Preferably, the carrier is suitable for intravenous, intramuscular, subcutaneous, parenteral, spinal or epidermal administration (e.g., by injection or infusion). The therapeutic compounds may include one or more pharmaceutically acceptable salts.

A "pharmaceutically acceptable salt" refers to a salt of the active ingredient. The salt form retains the desired biological activity of the parent compound and does not impart any undesired toxicological effects. The pharmaceutically acceptable salt may be an inorganic acid salt, an organic acid salt, or a metal salt.

One aspect of this patent document provides a formulation for topical delivery of a therapeutic agent. The formulation generally includes a macrolide immunosuppressant or a mTOR inhibitor ranging from about 0.01% to about 15% by weight in the formulation, and a solvent ranging from about 1% to about 99% by weight in the formulation. The solvent is capable of dissolving the macrolide immunosuppressant, and less than 4% of the macrolide immunosuppressant degraded in the formulation within 2 months. The formulation can be in a liquid or semi-solid state and an extended shelf-life, which overcomes instability of conventional dosage forms when exposed to solvents. Non-limiting examples of the macrolide immunosuppressant include tacrolimus, pimecrolimus, sirolimus, acsomycin, everolimus, and pharmaceutically acceptable salts thereof. The formulation can be in the form of a solution, a foam, a spray, a gel, an ointment, a cream, or an aerosol.

Both sirolimus and everolimus are mTOR inhibitors and each has three forms of isomers: isomer A, B and C. Isomer B is the pharmaceutical active form and will transform into A or C under dissolved state. Isomer C refers to the oxepane isomer of sirolimus or everolimus. Seco-Rapamycin is another isomer and degradation product that can be formed from isomer B of sirolimus.

For sirolimus, isomer B is the predominant isomer and contains an intra molecular kemiketal, forming a six-membered ring. Isomer C can be formed from isomer B and also contains an intra molecular kemiketal but with a neighboring keto group and thus forming a seven-membered ring (oxepane) in its structure. Sirolimus isomer B and isomer C have the following structures:

Sirolimus Isomer B

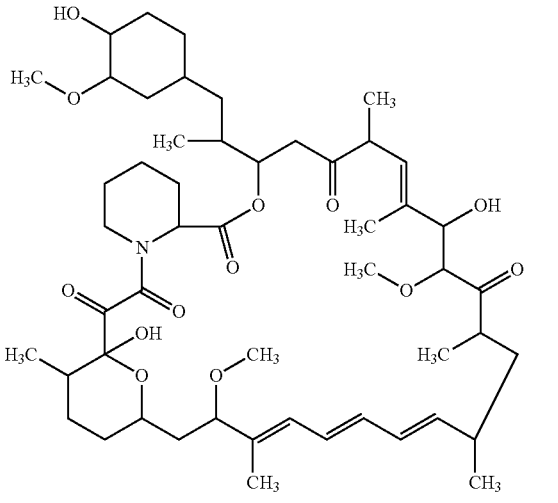

Sirolimus Isomer C

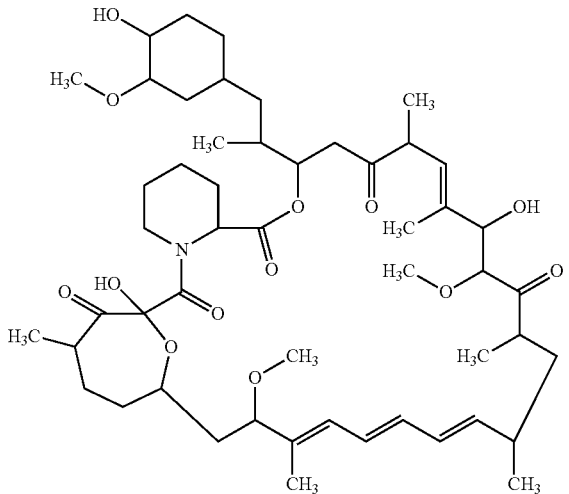

Isomer B of everolimus can similarly convers to isomer C. The formulation disclosed herein minimizes the conversion into undesirable isomers (e.g. isomer A, C and Seco-Rapamycin) of sirolimus or everolimus and maintains the agent in their therapeutically effective form for an extended period of time. In exemplary embodiments of the formulation described herein, while an undesirable isomer may be present initially (hour 0) in the formulation, less than about 0.1%, less than about 0.2%, less than about 0.3%, less than about 0.4%, less than about 0.5%, less than about 0.8%, less than about 1%, less than about 2%, less than about 3%, less than about 4%, less than about 5%, less than about 6%, less than about 7%, less than about 8%, less than about 9%, or less than about 10% of sirolimus or everolimus converts thereafter from isomer B to isomer A, C or Seco-Rapamycin of sirolimus or everolimus in or after about 1 week, 2 weeks, 1 month, 2 months, 3 months, 4 months, 5 months, 6 months, 12 months, 1 year, 2 years, 3 years or 4 years at controlled room temperature or under refrigerated condition of 2-8° C. In some embodiments, less than about 0.1%, less than about 0.15%, less than about 0.2%, less than about 0.4%, less than about 0.5%, less than about 0.8%, or less than about 1% of sirolimus converts or degrades from isomer B to Seco-Rapamycin in or after about 1 week, or 2 weeks from time 0. In some embodiments, less than about 0.2%, less than about 0.4%, less than about 0.5%, less than about 0.6%, less than about 0.8%, or less than about 1% of sirolimus converts from isomer B to isomer C in about 2 weeks from time 0. In some embodiments, less than about 0.2%, less than about 0.4%, less than about 0.5%, less than about 0.8%, less than about 1%, less than about 1.5%, less than about 2%, less than about 3%, or less than about 5% of sirolimus converts from isomer B to isomer C in about 4 weeks from time 0. In some embodiments, the ratio between DMSO and propylene carbonate is selected so that less than 1%, less than 2%, less than 4% or less than 5% of sirolimus converts to isomer C in about 2 weeks, about 4 weeks, about 1 year, about 3 years or about 4 years at about 5° C. at room temperature or under refrigerated storage condition (e.g. 2, 5 or 8° C.).

In some more examples of the presently disclosed formulations or methods, the amount of isomer C or Seco-Rapamycin is less than about 1%, less than about 2%, less than about 3%, less than about 4%, less than about 5%, less than about 6%, less than about 7%, less than about 8%, less than about 9%, or less than about 10% of the total amount of sirolimus or everolimus in or over a period of about 5 days, 1 week, 2 weeks, 3 weeks, 4 weeks, 1 month, 2 months, 3 months, 4 months, 5 months, 6 months, 7 months, 8 months, 9 months, 10 months, 1 year, 2 years, 3 years or 4 years at room temperature or under refrigerated storage condition (e.g. 2, 5 or 8° C.). In some embodiments, the amount of isomer C or Seco-Rapamycin increased by less than 0.1%, less than 0.2%, less than 0.5%, less than 0.8%, less than 1%, less than 3%, less than 5%, or less than 10% in or over a period of 1 hour, 5 hours, 10 hours, 24 hours, 1 week, 2 weeks, 4 weeks, 2 months, 6 months, 12 months, 1 year, 2 year, 3 years or 4 years. As further shown in the examples below, the formulation of this patent document exhibits excellent stability in terms of the small amount of undesirable isomers detected in 3 years or 4 years. The phrase "in a period of time" (e.g. in 4 weeks or 4 years) refers to "the period of time from now or from time o" (e.g. 4 weeks or 4 years from now or from time 0) when detecting the amount of the undesirable isomers.

In some embodiments, the formulation is in the form of a solution, a foam, a spray, a gel, an ointment, a cream, or an aerosol. Ointments are generally semisolids that contain little (e.g. less than 5%) or no water but include hydrocarbons, waxes, or polyols as the vehicle. Creams are semisolids containing either water-in-oil or oil-in-water emulsions or aqueous microcrystalline dispersions. Gels are transparent preparations containing cellulose ethers, Carbromer or other polymers in water or a water-alcohol mixture. Foam are objects formed by trapping pockets of gas in a liquid or solid containing active ingredient, which are aqueous and non-aqueous spray preparations for topical. Sprays are jets of liquid in fine drops, coarser than a vapor; produced by forcing the liquid from the minute opening of an atomizer, mixing it with air for topical application. Aerosol are pressurized dosage forms containing therapeutic active ingredients which upon actuation emit a fine dispersion of liquid and/or solid materials in a gaseous medium.

The topical formulation generally contains from about 0.01% to about 15%, all subranges included, by weight of the mTOR inhibitor and a dermatologically carrier. In some embodiments, the mTOR inhibitor ranges from about 0.01% to about 10%, from 0.001% to about 5%, from 0.001% to about 2%, from 0.05% to about 5%, from 0.05% to about 3%, from 0.05% to about 2%, from 0.05% to about 1.5%, from 0.05% to about 1%, from 0.1% to about 5%, from 0.1% to about 2%, from 0.1% to about 1%, from 0. 1% to about 0.5%, from 0.3% to about 2%, from 0.3% to about 1%, from 0.3% to about 0.8%, from 0.5% to about 2%, from 0.5% to about 1%, from about 0.05% to about 1%, from about 0.1% to about 1%, from about 0.1% to about 0,8%, from about 0.1% to about 0.6%, from about 0.1% to about 0.5%, from about 0.2% to about 0.5%, or from about 0.2% to about 0.4% by weight in the formulation. In some embodiments, the mTOR inhibitor is sirolimus or everolimus. In further exemplary embodiments, the formulation contains about by weight 0.01%, 0.03%, 0.05%, 0.08%, 0.1%, 0.13%, 0.15%, 0.18%, 0.2%, 0.23%, 0.25%, 0.28%, 0.3%, 0.35%, 0.4%, 0.45%, 0.5%, 0.55%, 0.6%, 0.65%, 0.7%, 0.75%, 0.8%, 0.9%, 1%, 1.1%, 1.2%, 1.3%, 1.4%, 1.5%, 1.6%, 1.7%, 1.8%, 1.9%, 2.0% of sirolimus or everolimus, which has isomer B as the only or dominant form.

The amount of the solvent in the composition may vary depending on factors such as the specific agent and the disease to be treated. The solvent not only serves the role of dissolving the therapeutic agent (e.g. sirolimus or everolimus) for formulation but also maintains the shelf stability of the agent. In some embodiments, the solvent is present in a range of from about 0.5%-50%, all subranges included. In some embodiments, the solvent ranges from about 0.5%-20%, from about 1% to about 10%, from about 1% to about 8%, from about 1% to about 5%, from about 1% to about 3%, from about 2% to about 10%, from about 2% to about 8%, or from about 2% to about 5%, in the formulation. In further exemplary embodiments, the solvent is present in about 0.5%, 1%, 1.5%, 2%, 2.5%, 5%, 7.5% or 10% by weight. Non-limiting examples of the solvent N-Methyl-2-pyrrolidone (NMP), dimethyl sulfoxide (DMSO), propylene glycol, propylene carbonate, Caprylocaproyl polyoxyl-8 glycerides, and any combination of two or more of the above.

The ratio between the mTOR inhibitor and the solvent ranges from about 1:1 to about 1:100, from about 1:10 to about 1:100, from about 1:10 to about 1:80, from about 1:10 to about 1:50, from about 1:5 to about 1:20, from about 1:5 to about 1:15, from about 1:8 to about 1:25, from about 1:10 to about 1:25, from about 1:10 to about 1:15, from about 1:20 to about 1:25, or from about 1:10 to about 1:20. In some more exemplary embodiments, the ratio between the active ingredient mTOR inhibitor and the solvent is 1:10, 1:11, 1:12, 1:13, 1:14, 1:15, 1:16, 1:17, 1:18, 1:19, 1:20, 1:21, 1:22, 1:23, 1:24, and 1:25. In some embodiments, the mTOR inhibitor is sirolimus or everolimus, each in the form of isomer B as the active ingredient.

In some embodiments, the formulation or the solvent contains less than 5%, less than 1%, less than 0.5%, less than 0.1%, less than 0.05%, less than 0.01% of water. In some embodiments, the ratio of the solvent and water in the formulation is more than 5:1, more than 8:1, more than 10:1, more than 15:1, more than 20:1, or more than 30:1. In some embodiments, the sirolimus or everolimus and the solvent are in a ratio ranging from about 1:5 to 1:25, from about 1:8 to 1:20 or from about 1:8 to 1:15.

In some embodiments of the topical formulation descried herein, the mTOR inhibitor is isomer B of everolimus. In some embodiments, the solvent includes 1, 2 3, or more of DMSO, NMP, dimethyl isosorbide (DMI), propylene glycol, glycerin, and propylene carbonate. In some embodiments, more than 50%, more than 60%, more than 70%, more than 80%, more than 90%, more than 95% of the solvent is one of NMP, DMSO, propylene glycol and propylene carbonate. In some embodiments, the solvent consists essentially of DMSO and propylene carbonate. In some embodiments, the solvent consists essentially of DMSO and NMP. In some embodiments, the solvent contains a combination of propylene carbonate and DMSO. In some embodiments, the solvent contains a combination of NMP and DMSO. In some embodiments, more than 70%, more than 80%, more than 90%, more than 95% of the solvent is propylene carbonate. In some embodiments, more than 50%, more than 60%, more than 70%, more than 80%, more than 85%, more than 90%, more than 95%, or more than 99% of the solvent is NMP. In some embodiments, the ratio between DMSO and propylene carbonate (weight by weight) or the ratio between DMSO and NMP in the solvent ranges from about 5:1 to about 1:20, from about 2:1 to about 1:10, from about 1:1 to about 1:20, from about 1:1 to about 1:15, from about 1:1 to about 1:10, from about 1:2 to about 1:10, from about 1:4 to about 1:10, from about 1:6 to about 1:10, from about 1:8 to about 1:10, or from about 1:7 to about 1:9. In some more exemplary embodiments, the ratio between DMSO and propylene carbonate or between DMSO and NMP or between DMSO and a combination of NMP and propylene carbonate in the solvent is about 1:1, about 1:2, about 1:3, about 1:4, about 1:5, about 1:6, about 1:7, about 1:8, about 1:9, about 1:10, about 1:11, about 1:12, about 1:13, or about 1:15.

In some embodiments of the topical formulation descried herein, the mTOR inhibitor is isomer B of sirolimus. In some embodiments of the topical formulation descried herein, the solvent includes 1, 2 3, or more of DMSO, propylene glycol, NMP, dimethyl isosorbide (DMI), propylene glycol, glycerin, and propylene carbonate. In some embodiments, more than 50%, more than 60%, more than 70%, more than 80%, more than 90%, more than 95% of the solvent is one of NMP, DMSO and propylene carbonate. In some embodiments, the solvent consists essentially of DMSO and propylene carbonate. In some embodiments, the solvent consists essentially of DMSO and NMP. In some embodiments, the solvent contains a combination of propylene carbonate and DMSO. In some embodiments, the solvent contains a combination of NMP and DMSO. In some embodiments, more than 70%, more than 80%, more than 90%, more than 95% of the solvent is propylene carbonate. In some embodiments, more than 50%, more than 60%, more than 70%, more than 80%, more than 85%, more than 90%, more than 95%, or more than 99% of the solvent is NMP. In some embodiments, more than 50%, more than 60%, more than 70%, more than 80%, more than 85%, more than 90%, more than 95%, or more than 99% of the solvent is DMSO. In some embodiments, the ratio between DMSO and propylene carbonate or the ratio between DMSO and NMP in the solvent ranges from about 5:1 to about 1:20, from about 2:1 to about 1:10, from about 1:1 to about 1:20, from about 1:1 to about 1:15, from about 1:1 to about 1:10, from about 1:2 to about 1:10, from about 1:4 to about 1:10, from about 1:6 to about 1:10, from about 1:8 to about 1:10, or from about 1:7 to about 1:9. In some more exemplary embodiments, the ratio between DMSO and propylene carbonate or between DMSO and NMP in the solvent is about 1:1, about 1:2, about 1:3, about 1:4, about 1:5, about 1:6, about 1:7, about 1:8, about 1:9, or about 1:10.

The formulation may contain one or more pharmaceutically or dermatologically acceptable carriers including for example, a surfactant, a polymeric thickening agent, an emollient, an emulsifier, a buffering agent, a penetration enhancer and/or an oleaginous ointment base. In some embodiments, the carrier is selected from emollient agent, emulsifying agent, thickening agent, preservative, permeation enhancer, and buffering agent. In some embodiments, the emollient agent of the said composition is white petrolatum. In some embodiments, the emollient agent of the said composition is mineral oil. In some embodiments, the emollient age of the said composition is a combination of white petrolatum and mineral oil. In some embodiments, the surfactant or emulsifying agent is PEG-8 Caprylic or caprylocaproyl polyoxyl-8 glycerides (Labrasol). In some embodiments, the thickening agent is glyceryl dibehenate (Compitrol 888 ATO) and the solvent is DMSO and propylene carbonate.

In some embodiments, the formulation contains a surfactant ranging from about 0.1% to about 10%, from about 1% to about 10%, from about 2% to about 8%, or from about 3% to about 6% by weight in the formulation. In some embodiments, the surfactant is caprylocaproyl polyoxyl-8 glycerides.

In some embodiments, the formulation contains a thickener ranging from about 0.1% to about 10%, from about 1% to about 10%, from about 1% to about 8%, from about 1% to about 5%, or from about 1% to about 3% by weight in the formulation. In some embodiments, the glyceryl dibehenate (Compitrol 888 ATO).

Non-limiting examples of polymers having surfactant or emulsifying properties include, but are not limited to hydrophobically modified polyacrylic acid commercially under the tradename Pemulen™ TR-I and TR-2 by Lubrizol Corp., water-soluble or water-swellable copolymers based on acrylamidoalkyl sulfonic acid and cyclic N-vinylcarboxamides commercially available under the tradename Aristoflex® AVC by Clariant Corporation; water-soluble or water-swellable copolymers based on acrylamidoalkyl sulfonic acid and hydrophobically modified methacrylic acid commercially available under the tradename Aristo ex® HMB by Clariant Corporation and a homopolymer of acrylamidoalkyl sulfonic acid commercially available under the tradename Granthix APP by Grant Industries, Inc. Another class of notable polymeric emulsifier includes hydrophobically-modified, crosslinked, anionic acrylic copolymers, including random polymers, but may also exist in other forms such as block, star, graft, and the like. In one embodiment, the hydrophobically modified, crosslinked, anionic acrylic copolymer may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least about 3 carbon atoms. Suitable emollient agents include, for example, vegetable oils, fats obtained from animals, semisolid hydrocarbons obtained from petroleum and the like. Examples of oleaginous ointment bases include white ointment, yellow ointment, cetyl esters wax, paraffin, petroltum, white petrolatum, white wax, yellow wax and the like and mixtures thereof. Non-limiting examples of polymers having thickening properties can include PEG-150 distearate, PEG-7 glyceryl cocoate, PEG 200 hydrogenated glyceryl palmitate, PEG-120 methyl glucose dioleate, carboxymethylene polymer, carboxyvinyl polymer, acrylates, Clo-C3O alkyl acrylate crosspolymers, and combinations thereof.

The penetration enhancer increases in the permeability of the skin to rise the rate at which the drug permeate into the skin. Exemplary penetration enhancers include, by way of example and without limitation, volatile organic solvents (e.g. alcohols such as ethanol), nonvolatile organic solvents (e.g. amides such as pyrrolidones; polyol ethers such as glycol ethers; polyols such as glycols; and derivatives thereof) and the like and mixtures thereof. More Examples of dermal penetration enhancers include fatty acids, fatty acid esters, fatty alcohols, terpenes, glycols and glycol esters, 1,3-dioxolanes, macrocylic ketones containing at least 12 carbon atoms, oxazolidinones and oxazolidinone derivatives, alkyl-2-(N,N-disubstituted amino)-alkanoate esters, (N,N-disubstituted amino)-alkanol alkanoates and mixtures thereof.

Non-limiting examples of the emollient include mineral oil, dimethicone, glycerin, isopropyl palmitate, propylene glycol, petrolatum, carnauba wax, cetyl alcohol, cetyl ester wax, cetostearyl alcohol, emulsifying wax, hydrous lanolin, lanolin, lanolin alcohols, microcrystalline wax, paraffin, stearic acid, stearyl alcohol, white wax, yellow wax, squalane, and any combination thereof.

In some embodiments, the surfactant is a polymer in an amount ranging from about 0.1% to about 10% by weight in the formulation. In some embodiments, the thickening agent is a polymer in an amount of about 0.1%-10% by weight of the formulation. In some embodiments, the ointment base ranges from about 20% to about 90% by weight of the formulation.

In some embodiments, the topical formulation is the form of an ointment. In some embodiments, the formulation contains isomer B of Sirolimus ranging from about 0.1% to about 0.5%, a solvent ranging from about 1% to about 10% or from about 4% to about 5% consisting essentially of DMSO and propylene carbonate in a ratio ranging from about 1:5 to about 1:10 (e.g. about 1:8), a surfactant (e.g. Labrasol) in an amount ranging from about 1% to about 10% (e.g. about 5%), a thickening agent (e.g. Compritol 888 ATO) in an amount ranging from about 1% to about 10% (e.g. about 2%), and an ointment base ranging from about 70% to about 80%.

Another aspect of this patent document provides a process for preparing the formulation described above. Development of such topical formulation requires introducing suitable solvent and related processing methods to dissolve and handle the active pharmaceutical ingredient (API). APIs such as Sirolimus and everolimus should have great solubility in such solvent so that the solution can ease further manufacturing. Meanwhile the processing methods may not cause any stability issues on sirolimus and everlimus so that further quality, efficacy and safety profile can be achieved. The method generally includes:

(a) dissolving a mOTR inhibitor in a solvent to form a solution; and
(b) mixing the solution with one or more pharmaceutically acceptable carriers.

The scope and composition of the mOTR inhibitor, the solvent and the pharmaceutically acceptable carriers are as described above.

In some embodiments, the one or more pharmaceutically acceptable carriers comprise an ointment bases selected from the group consisting of white ointment, yellow ointment, cetyl esters wax, paraffin, petroltum, white petrolatum, white wax, yellow wax, and any combination thereof. In some embodiments, one or more pharmaceutically acceptable carriers are prepared in a separate mixture or solution, which is then combined with the solution of the a mOTR inhibitor (e.g. sirolimus or everolimus). In some embodiments, the solvent is selected from the group consisting of N-Methyl-2-pyrrolidone (NMP), dimethyl sulfoxide (DMSO), propylene glycol, dimethyl isosorbide (DMI), glycerin, and propylene carbonate, and any combination thereof.

The solvent for dissolving the therapeutic agent (e.g. sirolimus or everolimus) may contain one, two, three or more organic components (e.g. DMSO, propylene carbonate). The agent can also be dissolved in one component with subsequent addition of an additional component. The solution containing the inert carriers or ingredients may be heated under elevated temperature. The amount or ratio is the same as in the above described formulations.

An exemplary embodiment is provided as follows:
1. Dissolve the active ingredient in a solvent to obtain solution I (the solvent contains DMSO, NMP, propylene carbonate or any combination thereof such as a combination of DMSO and propylene carbonate or a combination of DMSO and NMP with ratios as describe above);
2. Heat the rest of the ingredients or carriers to above room temperature (e.g. 70° C. to 90° C. to obtain solution II, then stirred at 400 rpm for 10 min;
3. Keep the same speed, let solution II cooled to 50-60° C., then add solution I to solution II, keep the same speed for 10 min at 50° C.;
4. The resulting solution was stirred at 300 rpm and cooled to room temperature (optional);
5. Fill the cooled solution to tubes or bottles.

The active ingredient, solvent and other excipients are as described above. A related aspect provides a formulation prepared according to the method described herein.

Another aspect of this patent document provides a method of treating a skin disease or condition such as tuberous sclerosis complex (TSC) related skin lesions especially facial angiofibromas. Due to availability of large surface area, easy accessibility, application dynamics and the non-invasive nature of the therapy, topical administration provides many advantages over conventional routes of administration. First, it bypasses the portal circulation and thereby the hepatic first pass metabolism. Second, topical delivery avoids the problems of variable systemic absorption and metabolism. Third, it potentially reduces gastrointestinal irritation associated with oral administration. Further, it avoids the risks and patient noncompliance associated with parenteral treatment. Given the underlying disease mechanism and literature reports using mTOR inhibitors such as rapamycin as a topical agent, the formulation of mTOR inhibitors disclosed herein is expected to provide superior clinical benefit in treating skin diseases or conditions such as TSC related facial angiofibromas.

The method includes applying topically the formulation disclosed herein on the skin area to be treated once or twice, or as needed daily to provide targeted, localized, effective concentrations of agents. The skin area may be on any part of a subject's body such as face, torso, and limbs. In some embodiments, the subject is a human. The exact dosage and frequency of administration may depend on the subject's specific condition and the agent. One skilled in the art can determine the suitable administration regimen in view of the formulation disclosed herein and the knowledge available in the relevant medical field (e.g. treatment of facial facial angiofibromas). Typical side effects of systemic administration are reduced because the agents are not administered systemically.

Non-limiting examples of topical disease or condition to be treated with the formulation disclosed herein include angiofibromas, atopic dermatitis, Pachyonychia Congenita, Anterior Uveitis, Port-Wine Stain, Oral Mucosal Disease Due to Graft-versus-host, Oral Lichen Planus, Cutaneous T-cell Lymphoma, Non-Melanomatous Skin Cancer, Sturge-Weber Syndrome, multiple endocrine neoplasia type 1 (MEN1), Birt-Hogg-Dubé Syndrome (BHDS), Crohn Disease, Vitiligo, Vulvar Lichen Sclerosus, Vernal Keratoconjunctivitis, Cutaneous Lupus Erythematosus, Severe Seborrheic Dermatitis, Psoriasis, Allergic Conjunctivitis, Prurigo Nodularis, Ulcerative Colitis, Pityriasis Alba, Psoriasis Vulgaris, Chronic Hand Dermatitis, Kaposi's sarcoma, and hemangiomas.

For each of the aforementioned diseases or conditions, the formulation may be administered topically once, twice, three time, 4 times or more a day, or as needed. Alternatively, the composition may be applied once every two, three, four days, or as needed. The actual amount and frequency of administering the composition may depend on the specific disease conditions and can be determined by one of ordinary skill in the art (e.g. a dermatologist) without undue experiment. In exemplary embodiments, the sirolimus or everolimus can be administered at a dose of from about 0.01 g to about 10 g per day in the above composition.

EXAMPLES

The following examples are provided to enable one skilled in the art to practice the invention and are merely illustrative of the invention. The examples should not be read as limiting the scope of the invention as defined in the claims.

Example 1

Ointment—Formula Composition I

This example evaluated sirolimus and everolimus solubility and stability in various FDA approved topical solvents and co-solvent systems such as diethylene glycol monoethyl ether (Transcutol® P as manufactured by Gattefosse), N-Methyl-2-pyrrolidone (NMP), dimethyl sulfoxide (DMSO), ethanol, Caprylocaproyl polyoxyl-8 glycerides (Labrasol® as manufactured by Gattefosse) and propylene carbonate combined or alone.

In Transcutol P, sirolimus solubility is greater than 80 mg/ml under both room temperature and refrigerated condition and everolimus solubility is greater than 100 mg/ml under both room temperature and refrigerated condition. In NMP, sirolimus solubility is greater than 100 mg/ml under both room temperature and refrigerated condition and everolimus solubility is greater than 100 mg/ml under both room temperature and refrigerated condition. In DMSO, sirolimus solubility is greater than 100 mg/ml under room temperature and everolimus solubility is greater than 200 mg/ml under room temperature. The melting point of DMSO is 19° C. (66° F.; 292 K), thus it will freeze under refrigerated condition. In propylene carbonate, sirolimus solubility is around 30 mg/ml under both room temperature and refrigerated condition and everolimus solubility is greater than 100 mg/ml under both room temperature and refrigerated condition.

TABLE 1

| Ingredients | Function | % w/w |
| --- | --- | --- |
| Sirolimus | API | 0.1 |
| Mineral Oil | Emollient | 10.0 |
| White Petrolatum | Ointment base | 82.9 |
| Compritol 888 ATO | Thickener | 2.0 |
| DMSO | Solvent | 2.5 |
| Propylene Carbonate | Solvent | 2.5 |
| Total | | 100.0 |

The ointment composition of the example is prepared as follows:

1. Dissolve sirolimus in DMSO and propylene carbonate as solution I;
2. Heat mineral oil, white petrolatum and Compritol 888 ATO at 70° C. to 75° C. to make a solution, then stirred at 400 rpm for 10 min, as solution II;
3. Keep the same speed, let solution II cooled to 50° C., then add solution I to solution II, keep the same speed for 10 min at 50° C.;
4. The resultant solution was stirred by 300 rpm to be cooled to room temperature;
5. Fill the cooled solution to tubes or bottles.

Example 2

Ointment—Formula Composition II

TABLE 2

| Ingredients | Function | % w/w |
| --- | --- | --- |
| Everolimus | API | 0.4 |
| Mineral Oil | Emollient | 10.0 |
| Labrasol | Emulsifier | 5.0 |
| White Petrolatum | Ointment base | 77.6 |
| Compritol 888 ATO | Thickener | 2.0 |
| DMSO | Solvent | 5.0 |
| Total | | 100.0 |

The formulation of this example was prepared in substantially the same manner as the composition of Example 1 except that solution I was everolimus dissolved in DMSO.

Example 3

Ointment—Formula Composition III

TABLE 3

| Ingredients | Function | % w/w |
| --- | --- | --- |
| Everolimus | API | 0.4 |
| Mineral Oil | Emollient | 10.0 |
| Labrasol | Emulsifier | 5.0 |
| White Petrolatum | Ointment base | 77.6 |
| Compritol 888 ATO | Thickener | 2.0 |
| Propylene Carbonate | Solvent | 5.0 |
| Total | | 100.0 |

The formulation of this example was prepared in substantially the same manner as the composition of Example 1 except that solution I was everolimus dissolved in propylene carbonate.

Example 4

Ointment—Formula Composition IV

TABLE 4

| Ingredients | Function | % w/w |
| --- | --- | --- |
| Sirolimus | API | 0.2 |
| Mineral Oil | Emollient | 10.0 |
| Labrasol | Emulsifier | 5.0 |
| White Petrolatum | Ointment base | 78.3 |
| Compritol 888 ATO | Thickener | 2.0 |
| DMSO | Solvent | 0.5 |
| Propylene Carbonate | Solvent | 4.0 |
| Total | | 100.0 |

The formulation of this example was prepared in substantially the same manner as the composition of Example 1

Example 5

Ointment—Formula Composition V

TABLE 5

| Ingredients | Function | % w/w |
| --- | --- | --- |
| Sirolimus | API | 0.4 |
| Mineral Oil | Emollient | 10.0 |
| Labrasol | Emulsifier | 5.0 |
| White Petrolatum | Ointment base | 78.1 |
| Compritol 888 ATO | Thickener | 2.0 |
| DMSO | Solvent | 0.5 |
| Propylene Carbonate | Solvent | 4.0 |
| Total | | 100.0 |

The formulation of this example was prepared in substantially the same manner as the composition of Example 1. The table shows the percentage of isomer C in the overall amount of everolimus at different time points.

Example 6

Everolimus Isomer C Concentrations (%) in Stability Study in Various Solvents

TABLE 6

| Isomer C level (%) | DMSO | Propylene Carbonate | NMP | Transcutol P | Ethanol |
|---|---|---|---|---|---|
| 0 h | 1.63 | 1.63 | 1.62 | 1.71 | 1.85 |
| 1 h | 1.67 | 1.84 | 1.76 | 3.78 | 2.66 |
| 2 h | 1.73 | 2.06 | 1.86 | 5.26 | 3.81 |
| 4 h | 1.86 | 2.47 | 1.99 | 6.43 | 5.40 |

Experiments were performed to study the stability of everolimus in Transcutol P, NMP, DMSO and propylene carbonate under 40° C. at concentration of 20 mg/ml and everolimus in Transcutol P, NMP, DMSO, ethanol, Labrasol and propylene carbonate under 50° C. at concentration of 80 mg/ml. DMSO and propylene carbonate exhibited excellent stabilizing effect for sirolimus and could be used as dissolving agents together or separately. DMSO, NMP and propylene carbonate stabilized sirolimus and everolimus and could be used as dissolving agents together or separately.

Everolimus concentrations are at 80 mg/ml in the solvent and co-solvent systems. The said solution was stored at 50° C. oven and samples were evaluated at time 0, 1 h, 2 h and 4 h.

All the solvent or co-solvent systems in table 6 provide relative stable environment for everolimus, even at high temperature and high concentration compared to solvents in table 6. The assay of everolimus isomer C increased less than 1.5% from 0 h to 4 h in DMSO, propylene carbonate and NMP.

Example 7

Sirolimus Isomer C Concentrations in Stability in Various Solvents Under 40° C. for 24 hr

TABLE 7

| Isomer C level (%) | Transcutol P | DMSO | Propylene Carbonate | 50% NMP + 50% DMSO | NMP |
|---|---|---|---|---|---|
| 0 h | 4.93 | 1.51 | 1.12 | 1.07 | 1.00 |
| 1 h | 7.11 | 1.23 | 1.12 | 1.15 | 1.02 |
| 4 h | 8.14 | 1.72 | 1.46 | 1.46 | 1.21 |
| 24 h | 8.18 | 2.50 | 2.77 | 1.46 | 1.46 |

Sirolimus concentrations are at 20 mg/ml in the solvent and co-solvent systems. The solution was stored at 40° C. oven and samples were evaluated at time 0, 1, 4 and 24 hours with HPLC analysis. The table shows the percentage of sirolimus isomer C in the overall amount of sirolimus at different time points.

Sirolimus is stable in solvent NMP, DMSO and propylene carbonate. Although there was a small amount of isomer C at time 0, less than 1.5% of sirolimus converted thereafter to isomer C in NMP, DMSO and propylene carbonate within 24 hours.

Example 8

Seco-Rapamycin in Various Solvent Under 40° C. for 24 hr

TABLE 8

| Isomer C level (%) | Transcutol P | DMSO | Propylene Carbonate | 50% NMP + 50% DMSO | NMP |
|---|---|---|---|---|---|
| 0 h | 0.20 | N.D. | N.D. | N.D. | N.D. |
| 1 h | 0.23 | N.D. | N.D. | N.D. | N.D. |
| 4 h | 0.76 | 0.23 | N.D. | 0.09 | 0.12 |
| 24 h | 1.06 | 0.44 | 0.08 | 0.13 | 0.26 |

N.D. Not Detectable

Seco-Rapamycin is a major decomposition product of sirolimus, the open ring conformation of Rapamycin (sirolimus), is also quantitated in the solvent systems. The concentration of Seco-Rapamycin for the solvent and cosolvent system are shown in Table 8. The table shows the percentage of Seco-Rapamycin in the overall amount of sirolimus at different time points. The initial concentrations of Seco-Rapamycin were undetectable in the tested samples. Less than 0.5% of sirolimus converted or degraded to Seco-Rapamycin in Propylene Carbonate, DMSO and NMP.

DMSO and propylene carbonate exhibited excellent stabilizing effect for sirolimus. However, propylene carbonate exhibits a relatively low solubility for Sirolimus, and DMSO has a relatively low freezing point at 19° C., which make these two individual solvents unsuitable as API solvent when used alone. Surprisingly, a solvent system consisting of DMSO and propylene carbonate effectively dissolved the active ingredient and maintained its stability in the formulation descried herein.

Example 9

Optimization of DMSO and Propylene Carbonate Ratio in Sirolimus Ointments by Evaluation of Isomer C and Seco-Rapamycin Concentrations on Stability

TABLE 9

| | Formulation | | | | |
|---|---|---|---|---|---|
| Ingredients | 0818-1 w/w % | 0819-1 w/w % | 0819-2 w/w % | 0928-1 w/w % | 0928-2 w/w % |
| Sirolimus | 0.2 | 0.2 | 0.2 | 0.2 | 0.4 |
| White Mineral Oil | 10 | 10 | 10 | 10 | 10 |
| Labrasol | 5 | 5 | 5 | 5 | 5 |

TABLE 9-continued

| Ingredients | Formulation | | | | |
|---|---|---|---|---|---|
| | 0818-1 w/w % | 0819-1 w/w % | 0819-2 w/w % | 0928-1 w/w % | 0928-2 w/w % |
| White Petrolatum | 77.8 | 77.8 | 72.8 | 78.3 | 78.1 |
| Compritol 888 ATO | 2 | 2 | 2 | 2 | 2 |
| DMSO | 2.5 | 1.0 | 5.0 | 0.5 | 0.5 |
| PC (Propylene Carbonate) | 2.5 | 4.0 | 5.0 | 4 | 4 |
| Seco-Rapamycin initial | 0 | 0 | 0 | 0 | 0.087 |
| Seco-Rapamycin 30° C./65% RH 1 w | 0.19 | 0.12 | 0.19 | | |
| Seco-Rapamycin 30° C./65% RH 2 w | 0.57 | 0.44 | 0.56 | 0.132 | 0.103 |
| Seco-Rapamycin 30° C./65% RH 4 w | | | | 0.267 | 0.195 |
| Seco-Rapamycin 25° C./60% RH 10 w | | | | 0.442 | 0.348 |
| Isomer C initial | 1.04 | 1.09 | 1.25 | 1.289 | 1.288 |
| Isomer C 30° C./65% RH 1 week | 2.32 | 2.12 | 2.27 | | |
| Isomer C 30° C./65% RH 2 weeks | 3.13 | 2.88 | 3.06 | 1.806 | 1.611 |
| Isomer C 30° C./65% RH 4 weeks | | | | 2.405 | 2.149 |
| Isomer C 25° C./60% RH10 weeks | | | | 2.551 | 1.810 |

The ratios of propylene carbonate and DMSO in the sirolimus ointment formulations were further evaluated as listed in Table 9. The DMSO and propylene carbonate ratio were evaluated at 2.5%:2.5%; 1.0%:4.0%; 5:0%:5:0% and 0.5%:4.0% (w/w) in the final formula, API was dissolved in the aforementioned solvent system and stability was evaluated at different conditions over 10 weeks period. Formulation with DMSO: propylene carbonate ratio at 0.5%:4% (0928-1 and 0928-2) showed best stability with Seco-Rapamycin concentration less than 0.5% and Isomer C less than 3% stored at 25° C./60% RH for 10 weeks. The HPLC chromatograms of Sirolimus Ointment showing the amounts of Sirolimus, Seco-Rapamycin and Isomer C are provided in FIG. 1.

Example 10

Stability of Sirolimus Ointment Stored at 5° C. (2-8° C.) for Up to 48 Months

TABLE 10

| Time Points | Initial | 12 Months | 24 Months | 36 Months | 48 Months |
|---|---|---|---|---|---|
| Sirolimus Ointment 0.4% Batch Number AFI2017092101 | | | | | |
| Description (White or off-white ointment) | Confirm | Confirm | Confirm | Confirm | Confirm |
| pH | 6.52 | 7.89 | 6.10 | 5.96 | 5.48 |
| Viscosity (cp) | 75900 | 76800 | 74300 | 86800 | 65500 |
| Sirolimus Assay (%) | 100.5 | 96.1 | 99.0 | 94.0 | 94.4 |
| Isomer C (%) | 3.04 | 2.84 | 2.87 | 3.61 | 3.88 |
| Sirolimus Ointment 0.2% Batch Number AFI2017092001 | | | | | |
| Description (White or off-white ointment) | Confirm | Confirm | Confirm | Confirm | Confirm |
| pH | 6.67 | 6.63 | 6.69 | 5.93 | 6.19 |
| Viscosity (cp) | 75800 | 78100 | 75300 | 79900 | 53800 |
| Sirolimus Assay (%) | 102.4 | 97.2 | 100.4 | 94.1 | 100.4 |
| Isomer C (%) | 2.95 | 3.05 | 3.27 | 4.22 | 4.35 |

Example 11

Sirolimus Ointment: 39-Week Dermal Dose Toxicity and Toxicokinetics Study in Minipigs Test article Sirolimus Ointment at three concentrations (0.2%, 0.4% and 0.8%) and vehicle control were administered to minipigs by dermal application once daily for up to 39 weeks. Repeated dermal application up to 13.6 mg/kg/day with 0.8% (w/w) Sirolimus Ointment or the vehicle to male and female minipigs once daily for 39 weeks was well tolerated and did not cause any adverse effect in mortality, clinical signs, skin reaction, body weight, food consumption, body temperature, ophthalmic examinations, electrocardiography, clinical pathology, organ weight alterations, macroscopic observations and microscopic observations. The no-observed-adverse-effect-level (NOAEL) was determined to be 13.6 mg/kg/day. At 13.6 mg/kg/day, the $C_{max}$ and $AUC_{0-24\ h}$ on Day 268 were 6.78±5.17 ng/mL and 74.4±9.03 h*ng/mL in males, 6.65±3.46 ng/mL and 121±67.4 h*ng/mL in females, respectively.

Example 12

A Phase 2, Multi-Center Prospective, Randomized, Double-Blind, Placebo-Controlled, Parallel-Design Study In a phase 2, multi-center prospective, randomized, double-blind, placebo-controlled, parallel-design study to evaluate the safety and efficacy of the topical formulation of Sirolimus for cutaneous angiofibromas in subjects with tuberous sclerosis complex (TSC). Subjects who met the study entry criteria were randomized 1:1:1 to receive 1 of 3 treatments: Sirolimus ointment 0.2%, Sirolimus ointment 0.4%, or placebo ointment. All randomized subjects applied study medication topically to the cutaneous angiofibromas on the face once daily before bedtime for 12 weeks. Subjects who complete the double-blind phase of the study, with an overall compliance rate >80% were offered entry into an open-label period for an additional 12 weeks with treatment of Sirolimus 0.2% ointment.

The primary efficacy endpoint was the proportion of subjects with a clinical response of treatment success at week 12. Treatment success is defined as at least a 2-grade improvement on the week 12 Investigator Global Assessment (IGA) (Table 11) of the facial skin lesions assessed by the site investigator.

TABLE 11

Investigator's Global Assessment (IGA)

| Description | Grade | Disease Status |
|---|---|---|
| Clear | 0 | Clear skin with no signs of erythema and no disease related lesions |
| Almost clear | 1 | Slight redness with few disease related lesions |
| Mild | 2 | Greater than Grade 1; definite redness with scattered, some disease related lesions |
| Moderate | 3 | Greater than Grade 2; marked redness, concentrated, many disease related lesions |
| Severe | 4 | Greater than Grade 3; Very bright redness, confluent, highly concentrated disease related lesions |
| Very severe | 5 | Greater than Grade 4; fiery redness, very extensive disease related lesions covering very large area of the face |

Preliminary results show in the double-blind phase, out of 24 randomized subjects the number (%) of subjects achieved at least 2-grade improvement in IGA at week 12 are 1 (14.3%), 2 (25.0%) and 0 in Sirolimus 0.2%, 0.4% and placebo arm respectively. In open-label phase, total of 19 subjects were with IGA assessment at week 24 (OL week 12), 7 (36.8%) subjects achieved at least 2-grade improvement (Table 12).

TABLE 12

Number (%) of subjects with clinical response by treatment in double-blind (DB) phase and open-label (OL) phase

| Visit | Clinical Response | Sirolimus 0.2% (N = 7) | Sirolimus 0.4% (N = 8) | Placebo (N = 9) | Total (N = 24) |
|---|---|---|---|---|---|
| Week 12 (DB Phase) | No | 6/7 (85.7%) | 6/8 (75.0%) | 9/9 (100.0%) | NA |
| | Yes | 1/7 (14.3%) | 2/8 (25.0%) | 0 | NA |
| Week 24 (OL week 12) | No | 4/6 (66.7%) | 5/6 (83.3%) | 3/7 (42.9%) | 12/19 (63.2%) |
| | Yes | 2/6 (33.3%) | 1/6 (16.7%) | 4/7 (57.1%) | 7/19 (36.8%) |

It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

The invention claimed is:

1. A formulation for topical delivery of a therapeutic agent, comprising:
   (a) a therapeutically effective amount of sirolimus, and
   (b) a solvent comprising dimethyl sulfoxide (DMSO) and propylene carbonate;
   (c) one or more pharmaceutically acceptable carriers, wherein the one or more pharmaceutically acceptable carriers comprise caprylocaproyl polyoxyl-8 glycerides ranging from about 1% to about 10% by weight in the formulation;
   wherein the DMSO and the propylene carbonate are in a ratio selected from a range of from about 1:1 to about 1:10 and, at a temperature of 30° C. and a humidity of 65%, less than 5% of isomer C is detected in the formulation in about 2 weeks or less than 0.8% seco-rapamycin is detected in the formulation in about 2 weeks, wherein the isomer C is represented by the structure below

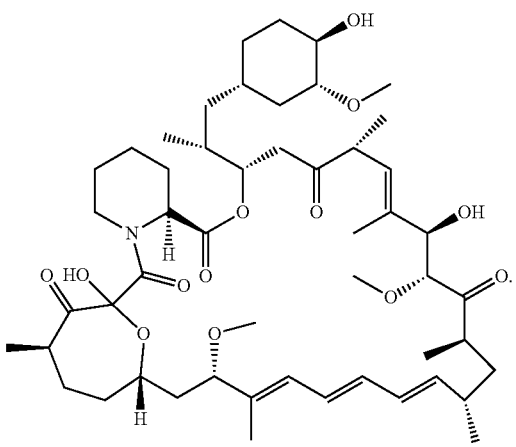

2. The formulation of claim 1, wherein less than 4% of isomer C is detected in the formulation in about 2 weeks.

3. The formulation of claim 1, wherein less than 5% of isomer C is detected in the formulation in about 3 years.

4. The formulation of claim 1, wherein the formulation comprises sirolimus in an amount ranging from about 0.05% to about 3% by weight.

5. The formulation of claim 1, wherein the solvent ranges from about 2% to about 10% by weight.

6. The formulation of claim 1, wherein the ratio between DMSO and propylene carbonate ranges from about 1:4 to 1:10 by weight.

7. The formulation of claim 1, wherein the formulation comprises sirolimus in an amount ranging from about 0.2% to about 0.4% by weight.

8. The formulation of claim 7, wherein the ratio between DMSO and propylene carbonate ranges from about 1:4 to 1:10 by weight.

9. The formulation of claim 7, wherein the ratio between DMSO and propylene carbonate is about 1:8 by weight.

10. The formulation of claim 1, wherein the ratio between sirolimus and the solvent ranges from about 1:10 to 1:100 by weight.

11. The formulation of claim 1, wherein less than 2% of sirolimus converts to isomer C in about 2 weeks and less than 0.4% of sirolimus converts to Seco-Rapamycin in about 2 weeks.

12. The formulation of claim 1, wherein less than 0.5% of sirolimus converts to seco-rapamycin in about 4 weeks.

13. The formulation of claim 1, wherein less than 2% of sirolimus converts to isomer C in about 4 weeks.

14. The formulation of claim 1, wherein less than 5% of sirolimus converts to isomer C in about 3 years at about 2-8° C.

15. The formulation of claim 1, wherein the one or more pharmaceutically acceptable carriers further comprise one or more agents selected from the group consisting of a polymeric thickening agent, an emollient, an emulsifier, a buffering agent, a penetration enhancer, and an ointment base.

16. The formulation of claim 1, wherein the one or more pharmaceutically acceptable carriers further comprise glyceryl dibehenate and mineral oil, wherein the glyceryl dibehenate ranges from about 1% to about 5% by weight in the formulation.

17. The formulation of claim 15, comprising the ointment base, wherein the ointment base ranges from about 20% to about 90% by weight in the formulation.

18. The formulation of claim 1, wherein the formulation is in a form of an ointment.

19. A method of treating a topical disease, comprising applying the formulation of claim 1 to a diseased skin area of a subject in need, wherein the topical disease is selected from the group consisting of angiofibromas, atopic dermatitis, Vitiligo, Cutaneous Lupus Erythematosus, and hemangiomas.

20. The formulation of claim 16, wherein the mineral oil is about 10% in the formulation.

* * * * *